United States Patent
Abedin et al.

(10) Patent No.: US 11,623,034 B2
(45) Date of Patent: Apr. 11, 2023

(54) SYSTEM AND METHOD TO LYSE AND REMOVE RED BLOOD CELLS FROM A CELL PRODUCT

(71) Applicant: Fenwal, Inc., Lake Zurich, IL (US)

(72) Inventors: Tanima J. Abedin, Chicago, IL (US); Alaina Schlinker, Chicago, IL (US); Jacintha Sales, Wauconda, IL (US)

(73) Assignee: Fenwal, Inc., Lake Zurich, IL (US)

(*) Notice: Subject to any disclaimer, the term of this patent is extended or adjusted under 35 U.S.C. 154(b) by 220 days.

(21) Appl. No.: 17/113,297

(22) Filed: Dec. 7, 2020

(65) Prior Publication Data

US 2021/0205525 A1    Jul. 8, 2021

Related U.S. Application Data (60) Provisional application No. 62/956,760, filed on Jan. 3, 2020.

(51) Int. Cl.
*A61M 1/36* (2006.01)
*A61M 1/34* (2006.01)

(52) U.S. Cl.
CPC ........ *A61M 1/3698* (2014.02); *A61M 1/3486* (2014.02); *A61M 1/3692* (2014.02); *A61M 2202/0429* (2013.01)

(58) Field of Classification Search
CPC .............. A61M 1/3698; A61M 1/3486; A61M 1/3692; A61M 2202/0429; A61M 1/0281;
(Continued)

(56) References Cited

U.S. PATENT DOCUMENTS 10,213,544 B2    2/2019   Radwanski
2008/0026451 A1*   1/2008   Braman ............. C12N 15/1006
                                                         435/270

FOREIGN PATENT DOCUMENTS

EP    2842619 A1    3/2015
WO   0204921 A2    1/2002
(Continued)

OTHER PUBLICATIONS

Xing Chen et al., Analytica Chimica Acta 584 (2007) 237-243. (Year: 2007).*
(Continued)

*Primary Examiner* — Pranav N Patel
(74) *Attorney, Agent, or Firm* — Cook Alex Ltd.

(57) ABSTRACT

A method is provided for removing red blood cells from a suspension comprising red blood cells, white blood cells, platelets and plasma using a spinning membrane separator. The method comprises: a) flowing whole blood into the gap of the spinning membrane separator; b) collecting red blood cells and white blood cells in the gap and passing plasma and platelets through the membrane; c) introducing a first quantity of lysing buffer into the gap; d) incubating the red blood cells, white blood cells and lysing buffer in the gap for a period of time to cause a lysis reaction with the red blood cells; e) introducing a second quantity of lysing buffer into the gap to displace the first quantity of lysing buffer and a first quantity of red blood cell debris out of the gap; f) introducing a first quantity of wash buffer into the gap to quench the lysis reaction and displace the second quantity of lysing buffer and a second quantity of red blood cell debris out of the gap; and g) introducing a second quantity of wash buffer into the gap to flow washed white blood cells out of the housing.

9 Claims, 10 Drawing Sheets

(58) Field of Classification Search
CPC . A61M 1/265; G01N 33/5002; C12N 5/0634; C12N 15/1003; C12N 1/06; C12N 15/1017; C12M 47/06; B01D 63/16; B01D 63/06; B01D 63/062; B01D 2315/02; B01D 33/06
See application file for complete search history.

(56) References Cited

FOREIGN PATENT DOCUMENTS

| WO | WO02/04921 A2 | 1/2002 |
| WO | WO02/004921 A3 | 1/2002 |
| WO | 2012125457 A1 | 9/2012 |
| WO | 2012125460 A1 | 9/2012 |
| WO | WO2012/125457 A1 | 9/2012 |
| WO | WO2012/125460 A1 | 9/2012 |
| WO | 2012154257 A1 | 11/2012 |
| WO | WO2012/154257 A1 | 11/2012 |
| WO | 2015067546 A1 | 5/2015 |
| WO | WO2015/067546 A1 | 5/2015 |

OTHER PUBLICATIONS

Gatza et al., Extracorporeal photophersis reverses experimental graft-versus-host disease through regulatory T-cells, The American Society of Hermatology, Blood, vol. 112, No. 4, pp. 1515-1521 (Aug. 15, 2008).
INCELL Corporation LLC, Innovative Life Science Solutions, ZAPR Red Blood Cell Lysing Buffer, Product Description, 2 pages, (2019).
European Patent Office, "Extended European Search Report", issued in connection with European application No. 20216919.9 dated May 17, 2021, 11 pages.
Extended European Search Report, counterpart EP Appl. No. 20216919.9 (dated May 17, 2021) (11 pages).

* cited by examiner

SYSTEM AND METHOD TO LYSE AND REMOVE RED BLOOD CELLS FROM A CELL PRODUCT

BACKGROUND

Cell therapy involves the administration of living cells that have been manipulated or processed ex vivo. In the manufacture of cellular therapies, there is a need to isolate certain cells to continue to work with the desired or target cell within that population.

The starting point for many cellular therapy manufacturing processes is an apheresis product. An apheresis product contains red blood cells (RBCs), a buffy coat layer (containing WBCs and platelets), and plasma. In many manufacturing processes, there is a specific type of WBC that needs to be isolated. RBCs and platelets interfere with many of the selection technologies, so removal of these cell types is often one of the first steps of the manufacturing processes.

Platelets can be removed by several established devices that use, for example, centrifuges or spinning membranes for separation. However, there are few methods available for RBC removal. One such method is the Ficoll-Paque gradient protocol, which uses Ficoll-Paque to create a density gradient of the apheresis product. This typically involves an operator using a pipette to manually remove the buffy coat layer that includes the WBCs from the gradient. This process is cumbersome, time consuming, and operator dependent.

Other methods include lysing the RBCs with lysing buffers, and then separating the RBC debris from the WBCs layer. This also has been a manual process, and one that may require a large volume of lysing buffer, as most lysing buffers require a high ratio of buffer to RBC cell suspension to properly lyse the RBCs. The larger the starting apheresis volume, the more lysing buffer is needed. Also, if WBCs are in contact with the lysing buffer for extended periods of time their structure can be harmed.

Therefore, there is a need to develop a method to remove RBCs from a cell product that requires less operator intervention and is susceptible to automation, has repeatable results, requires less material usage, and does not harm the target cells.

SUMMARY

The methods and systems described herein have several aspects. In a first aspect, a method is provided for removing red blood cells from a suspension comprising red blood cells, white blood cells, platelets and plasma. The method uses a spinning membrane separator that comprises a housing, a rotor rotatably supported within the housing, a membrane affixed to the rotor having a porous surface that permits plasma and platelets to pass therethrough but not red blood cells and white blood cells, with a gap being defined between the housing and the membrane.

The method comprises the steps of: a) flowing whole blood into the gap; b) collecting red blood cells and white blood cells in the gap and passing plasma and platelets through the membrane; c) introducing a first quantity of lysing buffer into the gap; d) incubating the red blood cells, white blood cells and lysing buffer in the gap for a period of time to cause a lysis reaction with the red blood cells; e) introducing a second quantity of lysing buffer into the gap to displace the first quantity of lysing buffer and a first quantity of red blood cell debris out of the gap and through the membrane; f) introducing a first quantity of wash buffer into the gap to quench the lysis reaction and displace the second quantity of lysing buffer and a second quantity of red blood cell debris out of the gap and through the membrane; and g) introducing a second quantity of wash buffer into the gap to flow washed white blood cells out of the housing.

In a related aspect, the spinning membrane separator comprises a housing having a first port/inlet, a second port/filtrate outlet and a third port/retentate outlet, and the method comprises the steps of a) flowing whole blood through the first port/inlet into the gap; b) closing the third port/retentate outlet and opening the second port/filtrate outlet to collect red blood cells and white blood cells in the gap and pass plasma and platelets through the membrane and out through the second port/filtrate outlet; c) flowing a first quantity of lysing buffer through the first port/inlet into the gap to displace the supernatant out through the second port/filtrate outlet; d) closing the second port/filtrate outlet and incubating the red blood cells, white blood cells and lysing buffer in the gap for a period of time to cause a lysis reaction with the red blood cells; e) opening the second port/filtrate outlet and flowing a second quantity of lysing buffer through the first port/inlet into the gap to displace the first quantity of lysing buffer and a first quantity of red blood cell debris out through the second port/filtrate outlet; f) flowing a first quantity of wash buffer through the first port/inlet into the gap to quench the lysis reaction and displace the second quantity of lysing buffer and a second quantity of red blood cell debris out through the second port/filtrate outlet; and g) closing the second port/filtrate outlet, opening the third port/retentate outlet, and flowing a second quantity of wash buffer through the first port/inlet into the gap to flow washed white blood cells out through the third port/retentate outlet.

In a second aspect, the method further comprises rotating the membrane at an idle speed during the incubation of the red blood cells, white blood cells and lysing buffer in the gap. Preferably, the idle speed is a rate of rotation of the membrane sufficient to gently mix the cells in the lysing buffer, and is a rate at which cells in the gap do not form Taylor vortices.

In a third aspect, the spinning membrane separator has a known interior volume, and the first and second volume of lysing buffer and the first volume of wash buffer is equal to the interior volume of the spinning membrane separator.

In a fourth aspect, the method comprises establishing a total time for steps c), d) and e) based on a time limit for exposure to lysing buffer recommended by a producer of the lysing buffer.

In a fifth aspect, a volume for the gap is established and the method comprises introducing whole blood into the gap until a packed cell volume of the whole blood reaches a predetermined percentage of the volume of the gap, based on the optimal ratio of lysing buffer to cells.

In a sixth aspect, a system is provided that includes a disposable fluid flow circuit including a spinning membrane separator and a reusable hardware component that includes a programmable controller programmed to automatically flow fluids through the spinning membrane separator and open and close the various ports to perform the methods of the aspects set forth above.

DETAILED DESCRIPTION

By way of the present application, a method and associated system are disclosed that provide for the automated removal of RBCs from a suspension, such as whole blood, that includes the target cells using a spinning membrane separator. The method generally involves first concentrating the RBCs in the gap between the spinning membrane and the separator housing, and then introducing the lysing buffer. More specifically, for the concentration step, spinning membrane filtration can be used to first concentrate the WBCs and RBCs. A filter membrane having a 4 um pore size can be used to filter out the supernatant, which would comprise platelets and plasma, from an apheresis product.

For the lysing application, the cells greater than 4 um are built up in the gap of the spinning membrane separator, and not permitted to exit the outlet port of the separator housing. Because the volume of the spinning membrane separator is a fixed, known volume, the volume of the apheresis product to be introduced into the spinning membrane separator for concentration is determined by using the cell concentration and volume input from the apheresis product. Consequently, the RBCs and WBCs are concentrated into a small volume.

Then the lysing buffer is introduced to fill the rest of the space within the spinner. The system is controlled so that the ratio of lysing buffer to RBC+WBC suspension meets the specifications of the manufacturer of the lysing buffer. For example, for ZAPR™ lysing buffer, manufactured by Incell Corporation of San Antonio, Tex., the recommended ratio of the volume of lysing buffer to the volume of the RBC pellet is 8-10:1. However, different lysing buffer manufacturers can recommend different volume to cell suspension ratios.

The suspension of lysing buffer, RBCs and WBCs is then incubated in situ in the spinning membrane separator to cause a lysis reaction with the RBCs. Additional lysing solution is then introduced into the separator to displace the spent lysing solution and RBC debris out of the gap. The total amount of time for the RBCs and WBCs to be exposed to the lysing buffer is dependent on the kind of lysing buffer used. A total residence time is typically recommended by the manufacturer, and the total time for exposure to lysing solution should be less than the total time recommended by the manufacturer in order to avoid damage to the WBCs. After the desired total exposure time has elapsed, a wash buffer is introduced into the separator to quench the lysis reaction and to displace the additional lysing buffer and RBC debris out of the gap. Additional wash buffer is then introduced into the gap to flow the washed WBCs out of the housing and into, e.g., a collection container.

Figure 1:
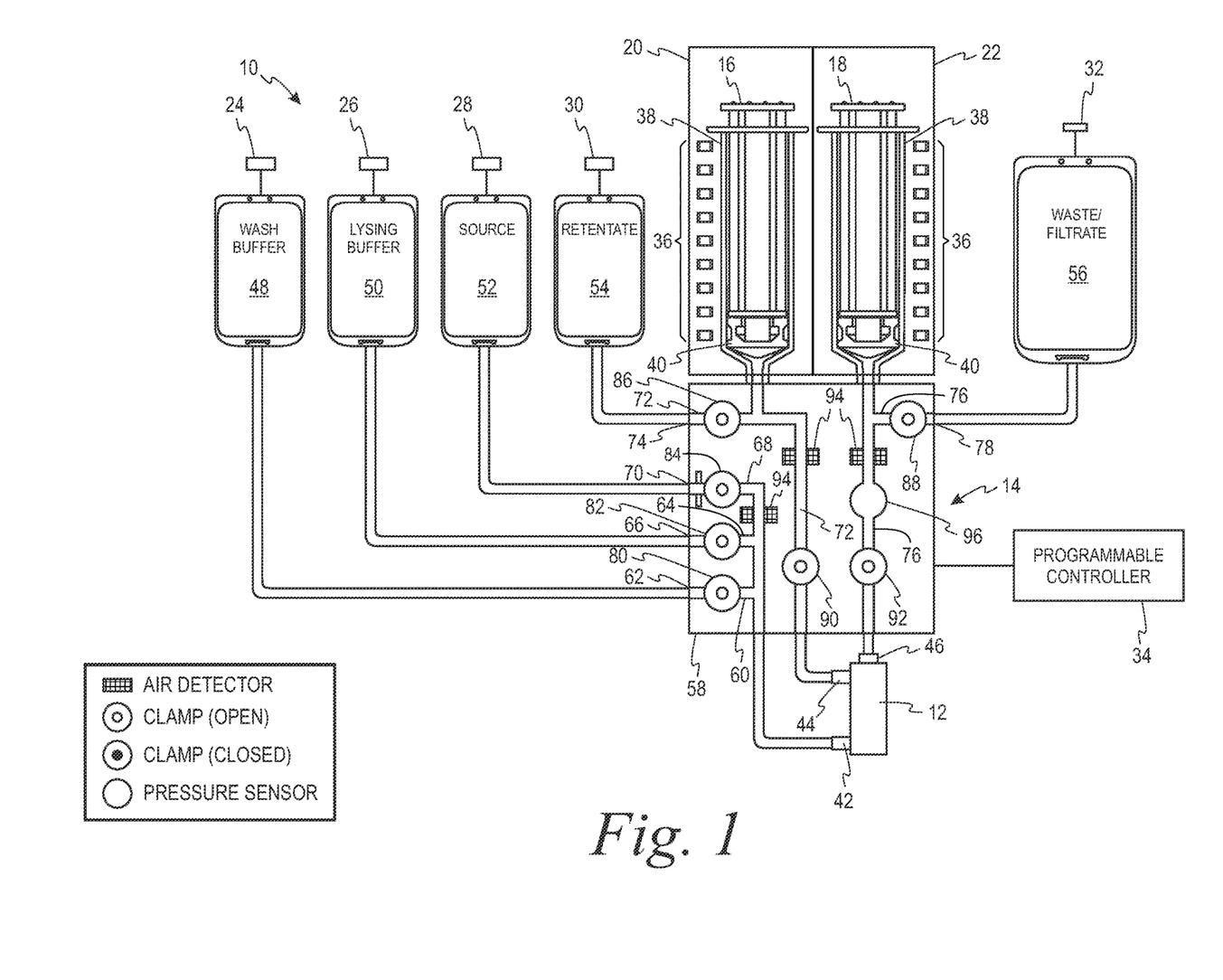
FIG. 1 is a schematic representation of a system including a spinning membrane separator for performing the automated removal of RBCs from a suspension such as whole blood in accordance with the present disclosure.

With reference to the drawings, FIG. 1 schematically illustrates a system generally designated 10, for performing the automated removal of RBCs from a suspension such as whole blood in accordance with the present disclosure. The system 10 includes a disposable fluid flow circuit and a reusable hardware component. The disposable fluid flow circuit includes a spinning membrane separator 12, such as is well known in the art, a cassette 14 for providing fluid management through the kit, and syringes 16 and 18 for moving fluid through the kit. An exemplary spinning membrane separator is shown and described in U.S. Pat. No. 9,381,291, which is incorporated herein by reference.

The reusable hardware component includes a drive system for the spinning membrane separator (not shown), syringe drivers/pumps 20, 22 for actuating the syringes 16, 18, respectively, weigh scales 24, 26, 28, 30 and 32, various actuators (not shown) for opening and closing valves/clamps associated with the cassette (described in greater detail below), and a programmable controller 34 for automatically operating the system.

The syringe drivers/pumps may be as described in U.S. 2018/0155070, incorporated herein by reference, and may include an array of position detectors 36 positioned along the length of the syringe barrel 38 that determine the position of the plunger head 40 of the syringe within the barrel of the syringe. The position detectors 36 are coupled to the controller 34 and may comprise transmitters that emit light and receivers that receive light reflected back to the receiver from the plunger head. This provides an indication of the volume of fluid moved by the syringe through the fluid flow circuit.

Returning to the fluid flow circuit, as illustrated, the spinning membrane separator 12 comprises a housing 12a having a rotor 12b rotatably mounted therein and to which a porous membrane is secured, with a gap 12c being defined between the interior surface of the housing 12a and the surface of the porous membrane. The housing 12a includes an inlet 42 through which the suspension of cellular material and other fluids are introduced into the separator 12, a first outlet 44 for flowing retentate (the target cells) out of the separator 12 and a second outlet 46 for flowing filtrate (waste) out of the separator 12. The disposable fluid flow circuit additionally includes a first container 48 for wash buffer, a second container 50 for lysing buffer, a third container 52 for the source suspension (e.g., previously collected whole blood from which the target cells are to be obtained), a fourth container 54 for receiving the retentate (i.e., the target cells), and a fifth container 56 for receiving the filtrate (i.e., the waste). These containers 48, 50, 52, 54 and 56 are supported by weigh scales 24, 26, 28, 30 and 32, respectively, which send signals to the controller 34.

Fluid management through the flow circuit is controlled by means of the cassette 14. The cassette 14 comprises a housing 58 having a series of fluid pathways therein interconnecting the various other components of the disposable kit. Each fluid pathway includes a flow control mechanism, such as valves or clamps, that are automatically operated by the controller based on signals received from the various detectors, sensors and scales of the system.

Specifically, the cassette 14 includes a first fluid pathway 60 with a first inlet 62 configured to be in fluid communication with the first container 48 (of wash media), a second fluid pathway 64 with a second inlet 66 configured to be in fluid communication with the second container 50 (of lysing buffer), a third fluid pathway 68 with a third inlet 70 configured to be in fluid communication with the third container 52 (of source material), a fourth fluid pathway 72 with a fourth inlet 74 configured to be in fluid communication with the fourth container 54 (for the retentate/target cells), and a fifth fluid pathway 76 with a fifth inlet 78 configured to be in fluid communication with the fifth container 56 (for the filtrate/waste).

Devices for selectively occluding the fluid pathways are associated with each of the fluid pathways for selectively occluding the fluid pathways. Such occluding devices may take the form of valves or clamps. A valve or clamp 80, 82, 84, 86 and 88 is respectively associated with each of the first, second, third, fourth and fifth inlets 62, 66, 70, 74, and 78 of the cassette 14. An additional valve or clamp 90, 92 is associated with each of the fourth and fifth flow paths 72, 76 to control flow out from the first and second outlets 44, 46 of the spinning membrane separator 12.

Sensors 94 are also provided that are able to detect differences in the fluid passing by. Specifically, the sensors 94 are able to detect interfaces between different types of fluids, such as an air-liquid interface, a wash media-retentate interface, and a wash media-filtrate interface. Upon detection of such interfaces, a signal is sent to the controller 34 that will act to control the configuration of the valves/clamps (open or closed) and actuate the syringe pumps to move fluid through the kit. The cassette may also include a pressure sensor 96 for monitoring purposes.

Operation of the system to provide a suspension of target cells substantially free of red blood cells will now be described. Once the fluid flow circuit is loaded onto the hardware component, with the containers of wash buffer, lysing buffer, and source media attached to their respective flow paths (the empty containers for the receipt of the retentate and waste may be pre-attached to the cassette), and all the containers are suspended on their weigh scales, the separation and collection procedure may commence. As is appreciated, the procedure is automatically controlled by means of the programmable controller, which sequentially operates the valves/clamps and the syringe pumps/drivers in accordance with signals received from the sensors.

The spinning membrane separator may first be primed (not shown), by flowing wash buffer therethrough. Then, the system is operated to introduce the source media into the spinning membrane separator, with the cellular material (red blood cells and white blood cells) being allowed to build up in the separator and the supernatant being drawn out of the separator. The amount of source media (whole blood) to be introduced into the spinning membrane separator may be a predetermined percentage of the volume of the gap in the spinning membrane separator between the housing and surface of the membrane, with whole blood being introduced into the gap of the spinning membrane separator until the packed cell volume of the whole blood reaches the predetermined percentage.

The total packed cell volume for a source media including red blood cells, white blood cells and platelets is as follows:

$$\text{Total WBC volume (mL)} + \text{Total RBC volume (mL)} + \text{Total PLT volume (mL)} = \text{Total Packed Cell Volume (mL)} \quad [1].$$

For the present purposes, the filter membrane of the spinning membrane separator will have a pore size of approximately 4 µm. As only white blood cells and red blood cells have cell diameters greater than (>) 4 µm, the packed cell volume of platelets is not considered, as the platelets will pass through the membrane along with the plasma. Thus, for a given volume of source media the total packed cell volume may be determined as follows:

$$\text{Total WBC volume (mL)} + \text{Total RBC volume (mL)} = \text{Packed Cell Volume (mL)} > 4 \text{ um} \quad [2].$$

The packed cell volume is a function of the concentration of white blood cells and red blood cells in the source media. The total WBC volume and RBC volume for a given volume of source media may be determined as follows:

$$\text{Source Volume(mL)} \times \text{WBC Concentration}\left(\frac{\text{cells}}{\text{mL}}\right) \times \frac{400 \text{ fL}}{\text{WBC Cell}} \times \frac{1 \text{ mL}}{1E12 \text{ fL}} = \text{Total WBC volume(mL), and} \quad [3]$$

$$\text{Source Volume(mL)} \times \text{RBC Concentration} \left(\frac{\text{cells}}{\text{mL}}\right) \times \frac{100 \text{ fL}}{\text{RBC Cell}} \times \frac{1 \text{ mL}}{1E12 \text{ fL}} = \text{Total RBC volume(mL)}. \quad [4]$$

By way of example, for a source media having a volume of 100 mLs with a WBC concentration of 10 E6 cells/mL and a RBC concentration of 10 E6 cells/mL, the packed cell volume may be calculated as follows:

$$100(\text{mL}) \times 10E6\left(\frac{\text{cells}}{\text{mL}}\right) \times \frac{400 \text{ fL}}{\text{WBC Cell}} \times \frac{1 \text{ mL}}{1E12 \text{ fL}} = 0.4 \text{ mL}, \quad [5]$$

$$100(\text{mL}) \times 10E6\left(\frac{\text{cells}}{\text{mL}}\right) \times \frac{100 \text{ fL}}{\text{RBC Cell}} \times \frac{1 \text{ mL}}{1E12 \text{ fL}} = 0.1 \text{ mL, and} \quad [6]$$

$$\text{Packed Cell Volume(mL)} > 4 \text{ um} = 0.4 \text{ mL} + 0.1 \text{ mL} = 0.5 \text{ mL}. \quad [7]$$

As can be appreciated, the volume of the gap of the spinning membrane separator must be sufficient to accommodate the packed cell volume of the red blood cells and white blood cells retained therein, plus the volume of lysing solution at the ratio recommended by the manufacturer.

Figure 2:
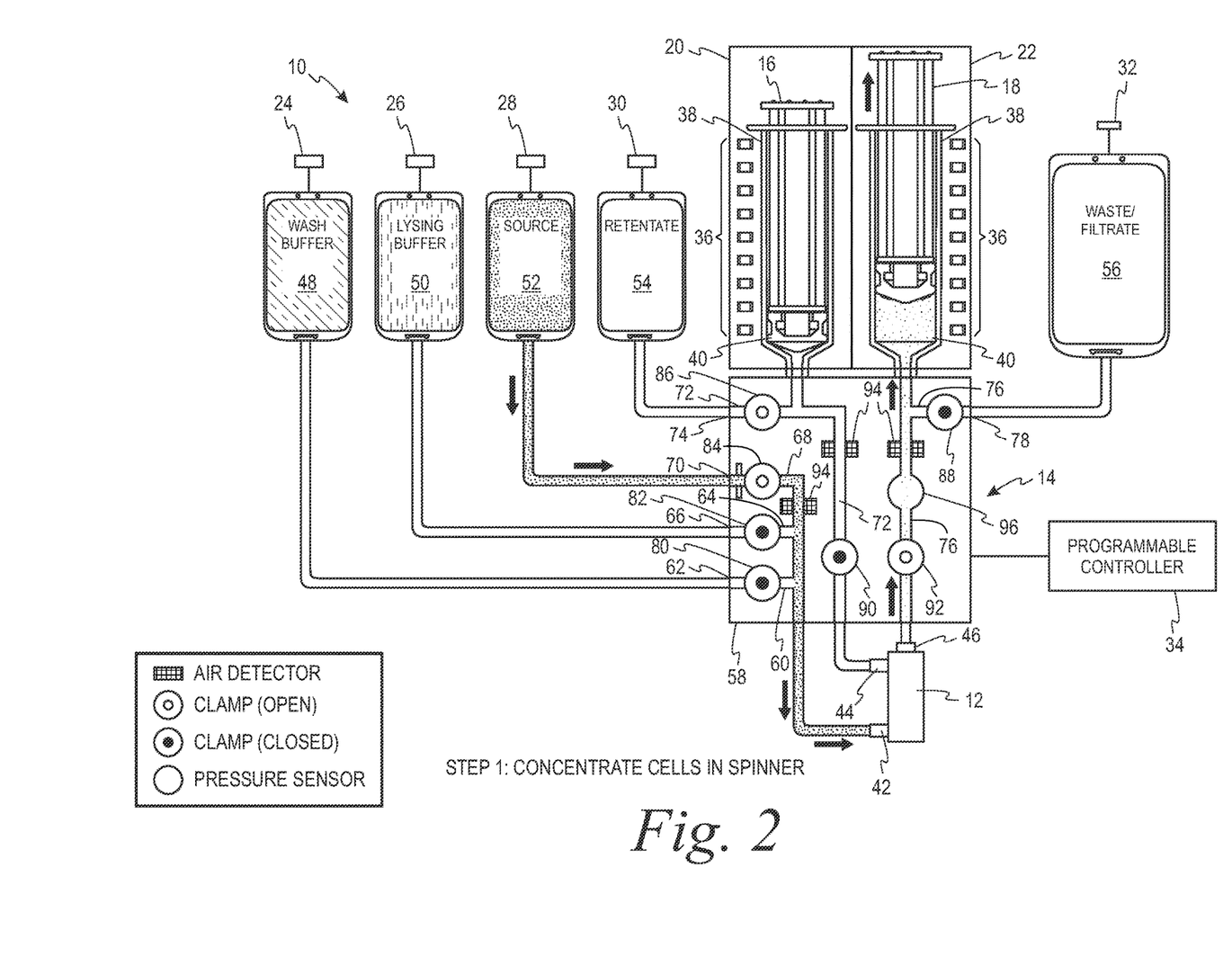
FIG. 2 illustrates the first step of the method in the context of the system shown in FIG. 1 in which cells are concentrated in the spinning membrane separator.

With reference to FIG. 2, clamps 80, 82, 88 and 90 are closed to prevent fluid flow through flow paths 60, 64 and 76. Clamps 84 and 92 are opened, and the syringe drive 22 is actuated to withdraw the plunger head 40 associated with syringe 18 to draw the source media out of the container 52 through the fluid flow path 68 and into the spinning membrane separator through the inlet 42. The cellular components, being unable to pass through the filter membrane, will build up in the gap between the membrane and the housing of the separator, while the supernatant (platelets and plasma) that passes through the membrane is flowed out through the outlet 46 of the spinning membrane separator 12 through the flow path 76 and into the barrel 38 of syringe 18. Once the desired volume of concentrated cells in the separator is obtained (discussed in greater detail below), the clamp 84 is closed.

Figure 3:
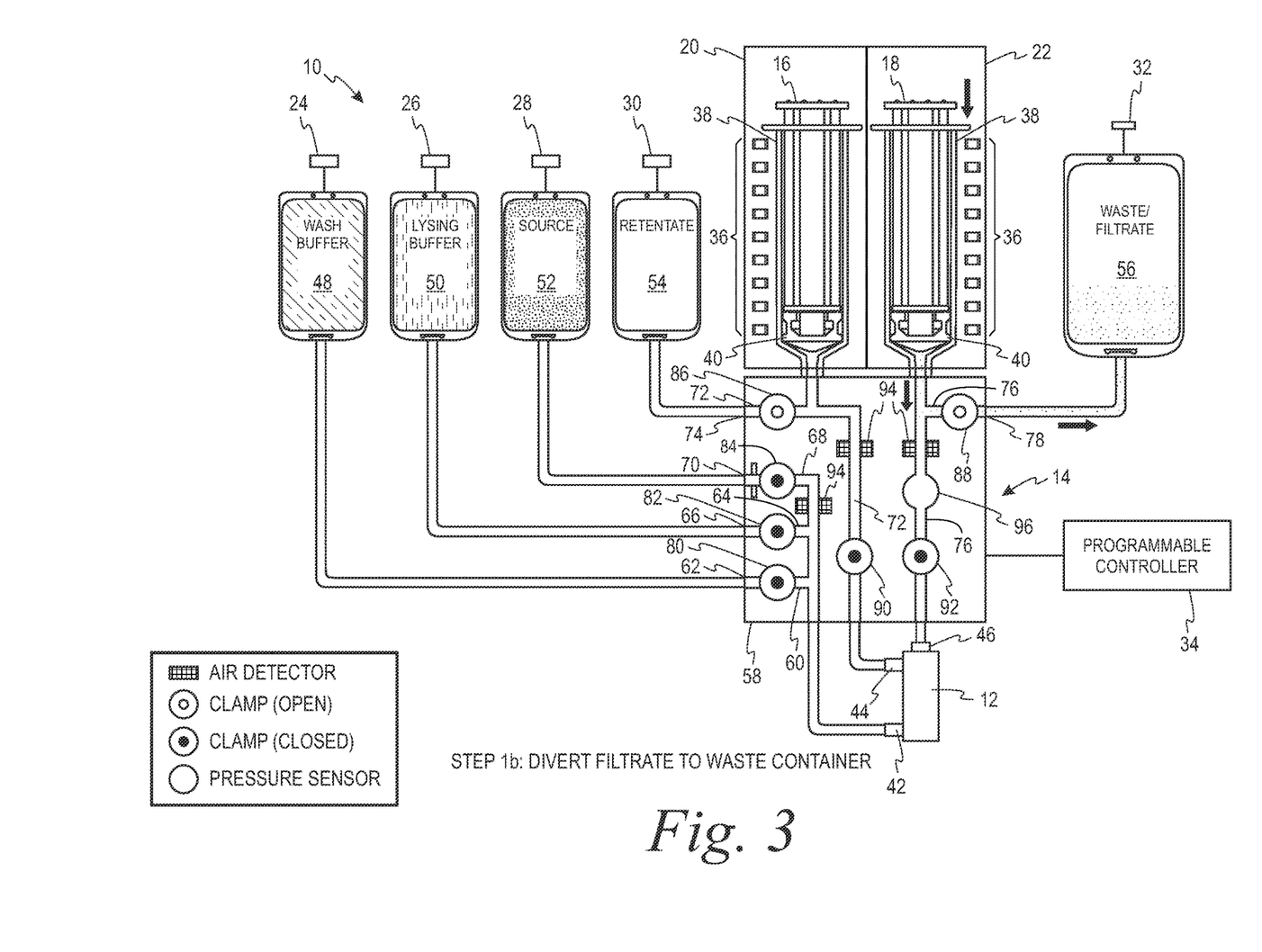
FIG. 3 illustrates an optional step that may follow the first step of FIG. 2 in which the filtrate or waste created in the first step is diverted to a waste container.

Optionally, and with reference to FIG. 3, the supernatant drawn into the syringe 18 may be flowed to the waste container 56. To this end, clamp 92 is closed and clamp 88 opened, and the syringe driver 22 actuated to return the plunger head 40 to its original position to flow the supernatant through the flow path 76 out of the cassette 14 through inlet 78 and into the container 56. This permits the full volume of the syringe to be available for receiving the lysing buffer and wash media generated in the subsequent steps of the method.

Figure 4:
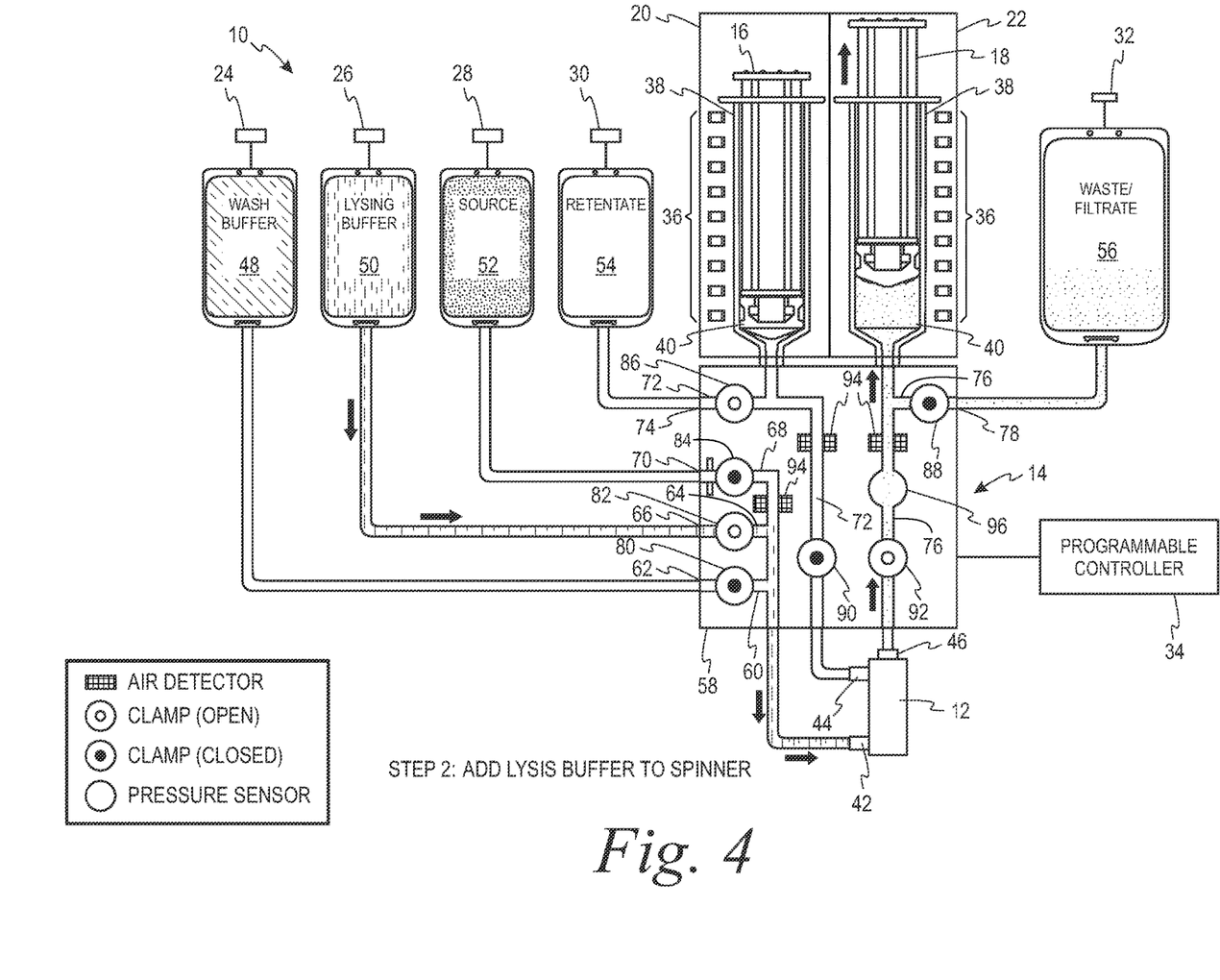
FIG. 4 illustrates the second step of the method in which lysing buffer is added to the spinning membrane separator.

With reference to FIG. 4, lysing buffer is then introduced into the spinning membrane separator 12 to wash out any supernatant (platelets and plasma) remaining on the separator after performing the steps illustrated in FIGS. 2 and 3. To this end, clamps 84 and 88 are closed, clamps 80 and 90 remain closed, clamp 82 is opened, and clamp 92 either remains open, if the step of FIG. 3 is not performed, or is opened, if the step of FIG. 3 is performed. The syringe driver 22 is then actuated to draw the plunger head 40 of syringe 18 into the barrel 38 of the syringe, thus drawing lysing solution out of the container 50, into the cassette 14 through inlet 66, through flow path 64 and into the spinning membrane separator through inlet 42. The lysing solution will displace the remaining platelets and plasma from the housing of the spinning membrane separator through the flow path 76 and into the barrel of the syringe 18. The quantity of lysing solution to be introduced into the separator will be predetermined and is a multiple of the volume of cells retained in the separator based upon the ration recommended by the producer of the lysing solution. In this regard, spinning membrane separator should be selected to have an interior volume that accommodates the total volume of the concentrated cells and the lysing solution. Optionally, the remaining platelets and plasma displaced by the lysing solution that is drawn into the syringe 18 may be flowed to the waste container 56, as described above with reference to FIG. 3.

Figure 5:
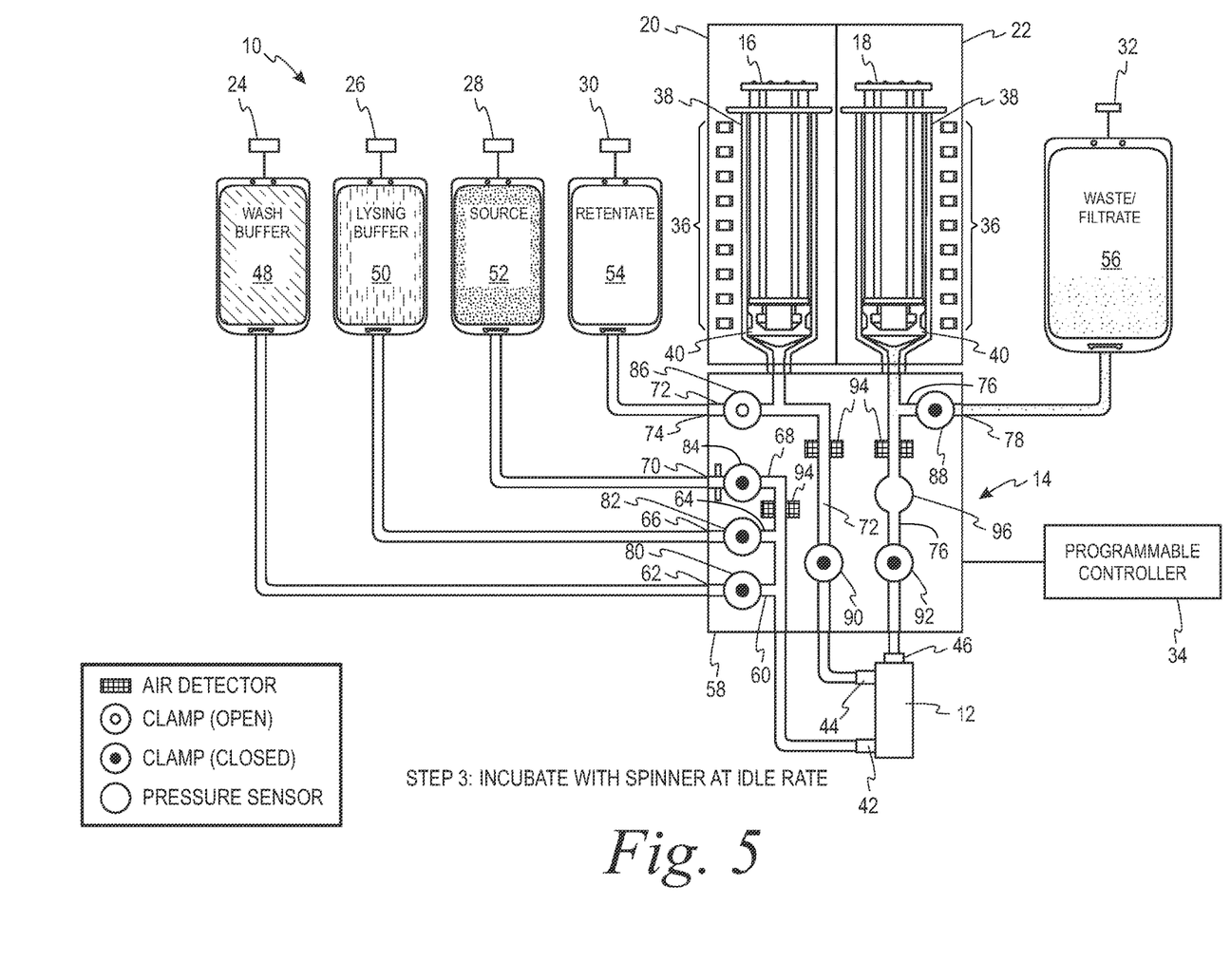
FIG. 5 illustrates the third step of the method in which the retained cells and lysing solution are incubated inside the spinning membrane separator.

The cells are then allowed to incubate in the lysing solution within the housing of the spinning membrane separator to cause a lysis reaction with the red blood cells. With reference to FIG. 5, clamps 82 and 92 are closed, while clamps 80, 84 and 90 remain closed, to retain the concentrated cells and lysing solution within the spinning membrane separator. During incubation, the membrane of the separator is preferably rotated at an idle speed, that being a rate of rotation below that at which Taylor vortices would be formed in the gap between the housing and the spinning membrane, to gently mix the cells in the lysing buffer.

The cells within the spinning membrane separator are then rinsed with lysing buffer to help ensure that the lysing buffer interacts with all of the red blood cells, as well as washing out the red blood cell debris that was generated. The red blood cell debris comprises fragments of the red blood cells which are of a size to pass through the membrane. To this end, and with reference to FIG. 6, clamps 80, 84, 88 and 90 remain closed, and clamps 82 and 92 are opened. The syringe driver 22 is then actuated to draw the plunger head 40 of syringe 18 further into the barrel 38 of the syringe, thus drawing lysing solution out of the container 50, into the cassette 14 through inlet 66, through flow path 64 and into the spinning membrane separator through inlet 42. The quantity of lysing buffer introduced during this rinsing step may be equal to the interior volume of the spinning membrane separator. Optionally, the lysing buffer and red blood cell debris displaced by the lysing solution that is drawn into the syringe 18 when the cells are rinsed with lysing buffer may be flowed to the waste container 56, as described above with reference to FIG. 3.

Figure 6:
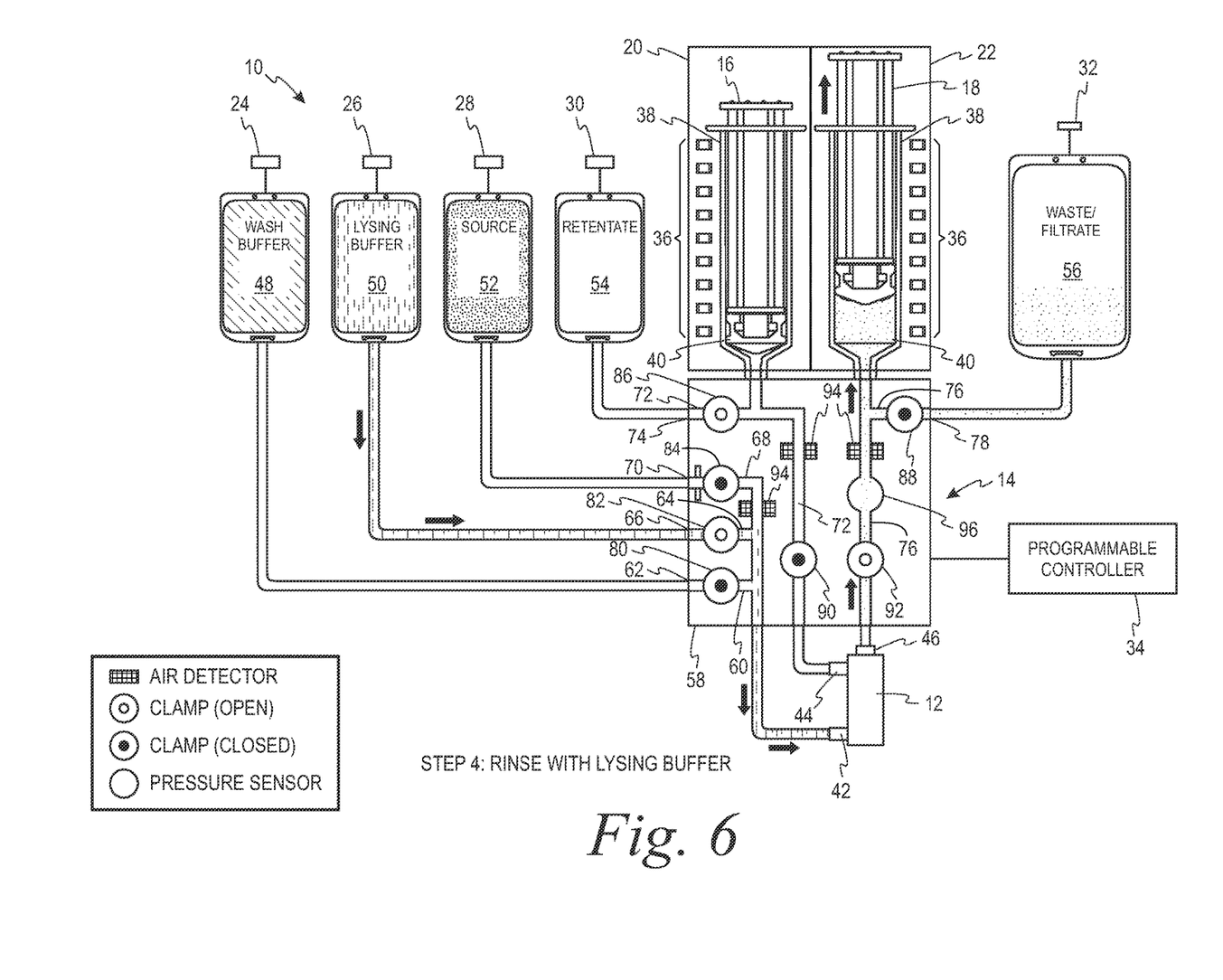
FIG. 6 illustrates the fourth step of the method in which the cells retained inside the spinning membrane separator are rinsed with lysing buffer.

The total time for performing the steps illustrated in FIGS. 4, 5 and 6, during which the concentrated cells retained in the spinning membrane separator are exposed to the lysing solution should be predetermined and based on a time limit exposure to lysing buffer recommended by the producer of the lysing buffer. This value can either be pre-programmed into the controller or input into the controller by the operator prior to commencement of the procedure.

Figure 7:
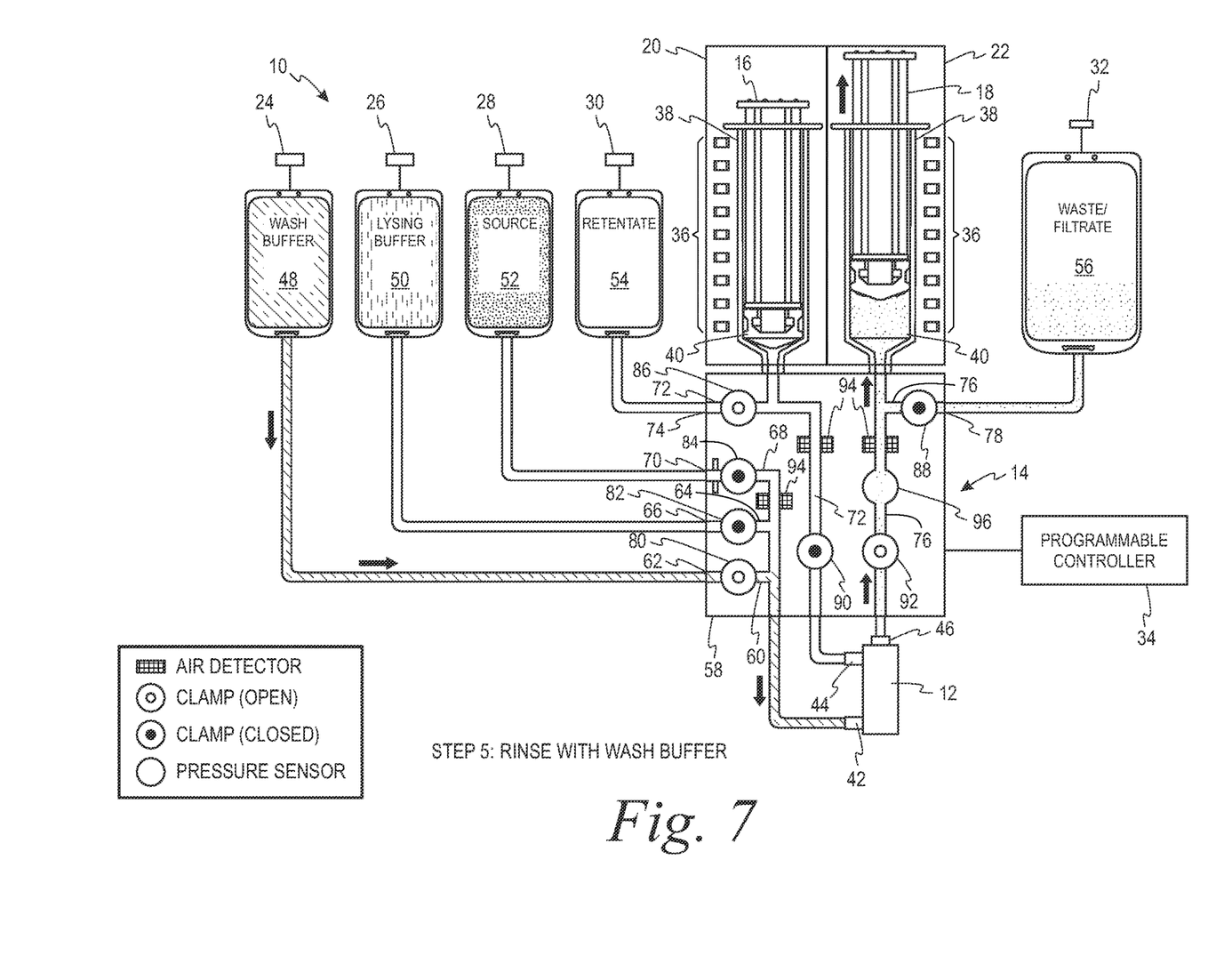
FIG. 7 illustrates the fifth step of the method in which the cells retained inside the spinning membrane separator are rinsed with a wash buffer.

Then, wash buffer is introduced into the spinning membrane separator to quench the lysis reaction and to further displace the red blood cell fragments and lysing buffer out of the separator. To this end, and as illustrated in FIG. 7, clamp 82 is closed and clamp 80 opened, while clamps 84, 88 and 90 remain closed, and the syringe driver 22 again actuated to further draw the plunger head 40 of syringe 18 further into the barrel 38 of the syringe, thus drawing wash buffer out of the container 48, into the cassette 14 through inlet 62, through flow path 60 and into the spinning membrane separator through inlet 42, with the lysing buffer used for rinsing being drawn into the barrel of the syringe 18. The quantity of wash buffer introduced during this rinsing step may be equal to the interior volume of the spinning membrane separator. Optionally, the lysing buffer displaced by the wash buffer that is drawn into the syringe 18 may be flowed to the waste container 56, as described above with reference to FIG. 3.

Figure 8:
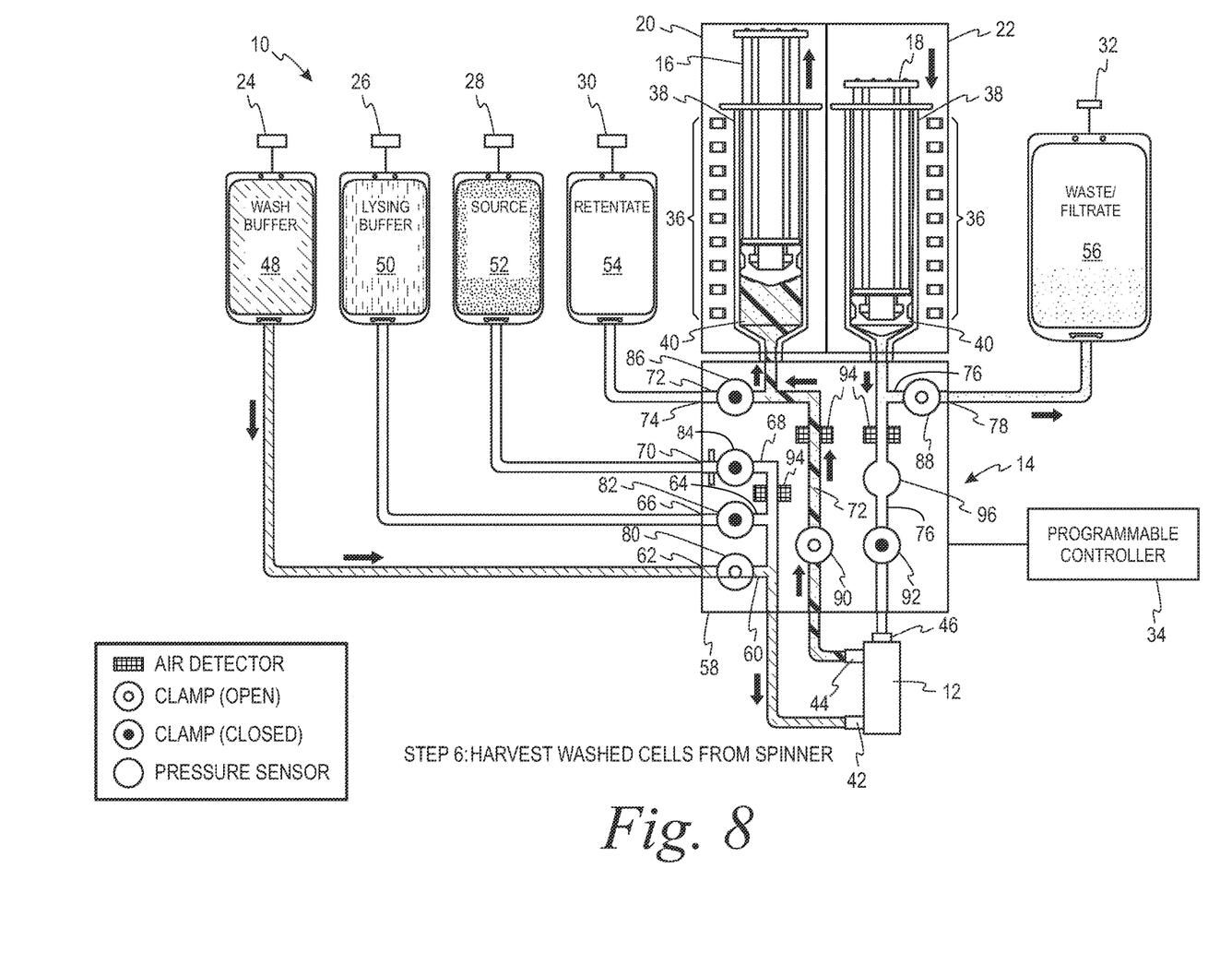
FIG. 8 illustrates the sixth step of the method in which the washed cells are harvested from the spinning membrane separator.

With reference to FIG. 8, the washed cells are then harvested from the spinning membrane separator into the syringe 16 by opening clamp 90 and closing clamps 86 and 92, while clamps 82 and 84 remain closed, and clamp 80 remains open. The syringe driver 20 is then actuated to draw the plunger head 40 of syringe 16 into the barrel 38 of the syringe, thus drawing additional wash buffer out of the container 48, into the cassette 14 through inlet 62, through flow path 60 and into the spinning membrane separator through inlet 42. The wash buffer displaces the washed cells out of the spinning membrane separator 12 through outlet 44, through flow path 72, and into the barrel of syringe 16. Wash buffer may be drawn from the container 48 until an interface between the washed cells and the wash buffer is detected by the interface detector 94 associated with flow path 72.

Figure 9:
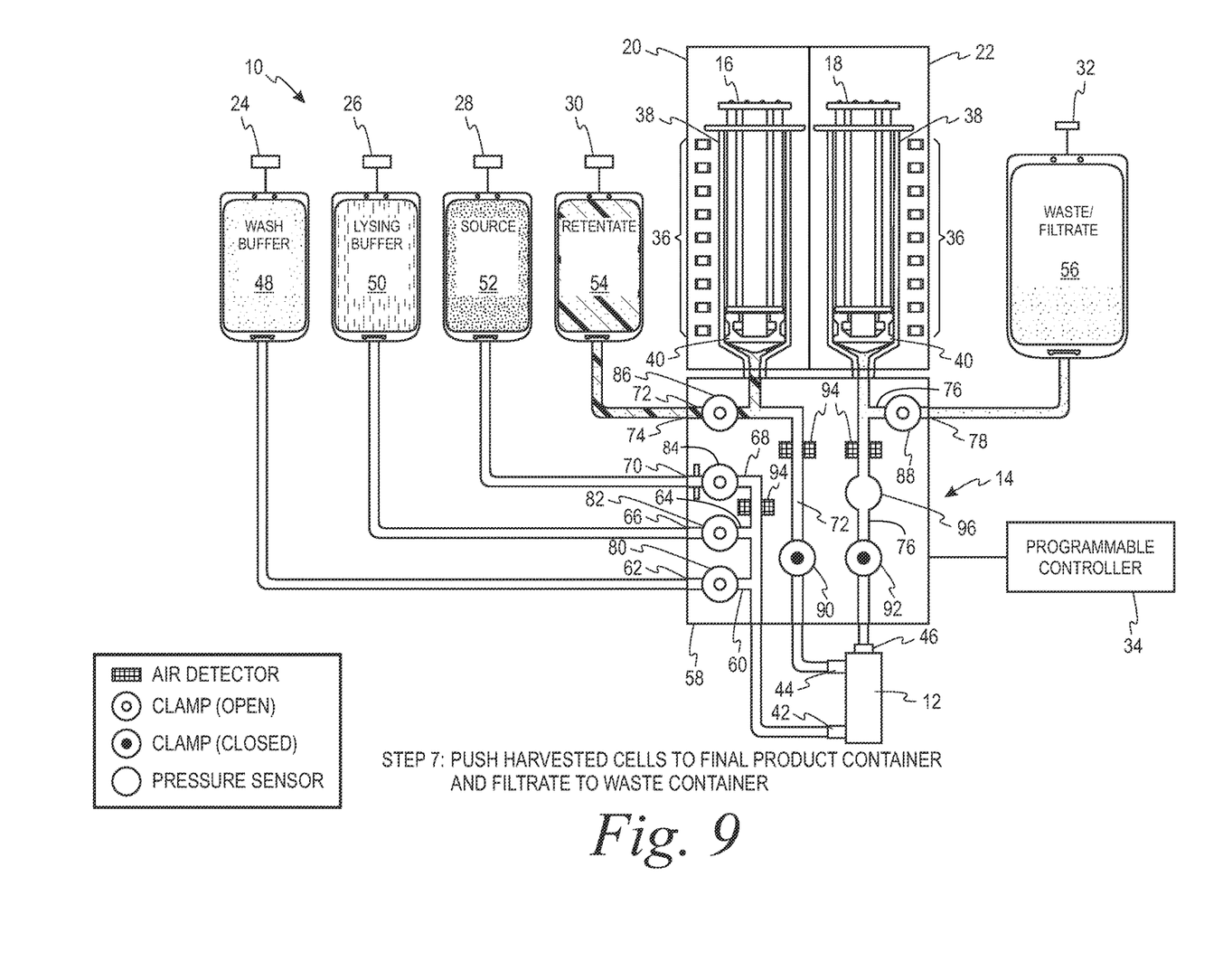
FIG. 9 illustrates a seventh step in which the harvested cells are pushed to the final product container and the filtrate is pushed to the waste container.
Figure 10:
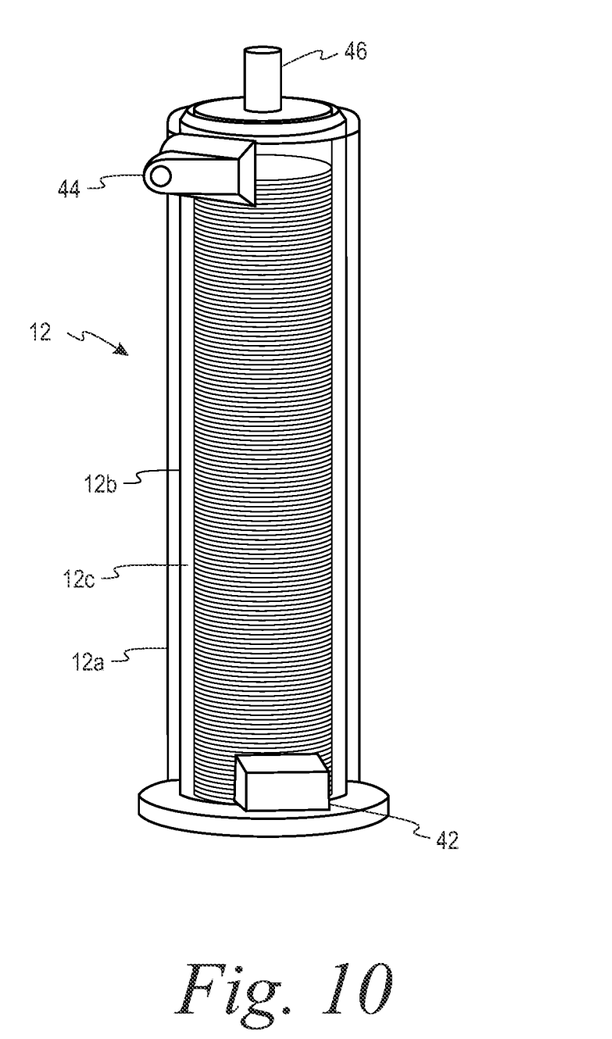
FIG. 10 is a perspective view of a spinning member separator enlarged to show detail.

Then, with reference to FIG. 9, the harvested cells are pushed to the collection container 54 by closing clamp 90, opening clamp 86, and actuating the syringe driver 20 actuated to return the plunger head 40 of syringe 16 to its original position to flow the washed cells through the flow path 72 out of the cassette 14 through inlet 68 and into the container 54. The harvested white blood cells, substantially free of any red blood cells, are then ready for further processing.

As can be appreciated, the volumes of fluid moved through the fluid flow circuit can be determined based on signals received from the weigh scales for the various containers and/or signals received from the position detectors for the plunger head associated with the syringe drivers and the interface detectors. Thus, with the programmer configured to receive signals from the weigh scales, position detectors, and interface detectors, the method is susceptible to automation, with the controller automatically opening and closing the appropriate clamps and actuating the syringe drivers based on such signals.

EXAMPLE

A hypothetical example follows, where the volume of the spinning membrane separator is 18 mLs, the apheresis volume is 100 mLs, the RBC hematocrit of the apheresis volume is 2% and the WBC concentration is 2.5E7 cells/mL.

The system first calculates the volume of cells concentrated and determines if that volume plus 5 times that volume can fit in the spinner (assuming that the recommended ratio of the volume of lysing buffer to the volume of the RBC cell suspension is 5:1. This multiplication factor must be configurable to accommodate for other lysing buffer types). With these inputs, the volume of RBCs present in the 100 mL apheresis is (100*0.02)=2 mL, while the total WBC volume is ~1 mL, using 400 fL as the average WBC cell volume. Therefore, total volume of concentrated RBCs and WBCs=3 mLs. The volume of lysing buffer needed to adequately lyse the RBCs is 5×3 mLs=15 mLs. Total volume is 18 mLs, which is the volume of the spinner. Therefore, the full 100 mLs will be pulled into the spinner and separated before the introduction of the lysing buffer.

Once the correct ratio of cells to lysing buffer is reached in the spinning membrane separator, the system shall incubate the suspension for a prescribed period. After this incubation period is reached in the spinner, a series of rinses to the spinning membrane separator is introduced. The initial rinse is done with lysing buffer to increase the probability of the buffer interacting with all of the RBCs. Some of the RBC fragments will wash through the 4 um pores with this rinse. The total amount of time of this rinse plus the incubation time shall be less than the residence time recommended by the lysing buffer manufacturer. Then, to stop the effects of the lysing buffer, a second rinse is done with a wash buffer which washes out any more RBC debris that was generated and any lysing buffer that remains in the cell suspension.

After the rinses are complete and the lysing buffer has been washed out, additional wash buffer is introduced into the spinning membrane separator to harvest the WBCs into the final product bag. As a consequence, less lysing buffer is used, operator intervention is reduced, and the time required will be less using this automated method when compared with manual lysing techniques.

Thus, a system and method for lysing and removing red blood cells from a cell product has been provided. It will be understood that the embodiment described above is illustrative of some of the applications of the principles of the present subject matter. Numerous modifications may be made by those skilled in the art without departing from the spirit and scope of the claimed subject matter, including combinations of features that are individually disclosed or claimed herein.

The invention claimed is:

1. A method for removing red blood cells from a suspension comprising red blood cells, white blood cells, platelets and plasma using a spinning membrane separator, the spinning membrane separator comprising a housing, a rotor rotatably supported within the housing, a membrane affixed to the rotor having a porous surface that permits plasma and platelets to pass therethrough but not red blood cells and white blood cells, with a gap being defined between the housing and the membrane, the method comprising:
   a) flowing whole blood into the gap;
   b) collecting red blood cells and white blood cells in the gap and passing plasma and platelets through the membrane;
   c) introducing a first quantity of lysing buffer into the gap;
   d) incubating the red blood cells, white blood cells and lysing buffer in the gap for a period of time to cause a lysis reaction with the red blood cells;
   e) introducing a second quantity of lysing buffer into the gap to displace the first quantity of lysing buffer and a first quantity of red blood cell debris out of the gap and through the membrane;
   f) introducing a first quantity of wash buffer into the gap to quench the lysis reaction and displace the second quantity of lysing buffer and a second quantity of red blood cell debris out of the gap and through the membrane; and
   g) introducing a second quantity of wash buffer into the gap to flow washed white blood cells out of the housing.

2. A method for removing red blood cells from a cell product using a spinning membrane separator, the spinning membrane separator comprising a housing having a first port/inlet, a second port/filtrate outlet and a third port/retentate outlet, a rotor rotatably supported within the housing, a membrane affixed to the rotor having a porous surface that permits supernatant/plasma and platelets to pass to pass therethrough but not red blood cells and white blood cells, with a gap being defined between the housing and the membrane, the method comprising:
   a) flowing whole blood through the first port/inlet into the gap;
   b) closing the third port/retentate outlet and opening the second port/filtrate outlet to collect red blood cells and white blood cells in the gap and pass plasma and platelets through the membrane and out through the second port/filtrate outlet;
   c) flowing a first quantity of lysing buffer through the first port/inlet into the gap to displace the supernatant out through the second port/filtrate outlet;
   d) closing the second port/filtrate outlet and incubating the red blood cells, white blood cells and lysing buffer in the gap for a period of time to cause a lysis reaction with the red blood cells;
   e) opening the second port/filtrate outlet and flowing a second quantity of lysing buffer through the first port/inlet into the gap to displace the first quantity of lysing buffer and a first quantity of red blood cell debris out through the second port/filtrate outlet;
   f) flowing a first quantity of wash buffer through the first port/inlet into the gap to quench the lysis reaction and displace the second quantity of lysing buffer and a second quantity of red blood cell debris out through the second port/filtrate outlet; and
   g) closing the second port/filtrate outlet, opening the third port/retentate outlet, and flowing a second quantity of wash buffer through the first port/inlet into the gap to flow washed white blood cells out through the third port/retentate outlet.

3. The method of claim 1 further comprising rotating the membrane at an idle speed during the incubation of the red blood cells, white blood cells and lysing buffer in the gap.

4. The method of claim 3 wherein the idle speed is a rate of rotation of the membrane at which cells in the gap do not form Taylor vortices.

5. The method of claim 1 wherein the spinning membrane separator has a known interior volume, and the first and second volume of lysing buffer and the first volume of wash buffer is equal to the interior volume of the spinning membrane separator.

6. The method of claim 1 further comprising establishing a total time for steps c), d) and e) based on a time limit for exposure to lysing buffer recommended by a producer of the lysing buffer.

7. The method of claim 1 wherein a volume for the gap is established and whole blood is introduced into the gap until a packed cell volume of the whole blood reaches a predetermined percentage of the volume of the gap.

8. A system for lysing and removing red blood cells from a cell product comprising a disposable fluid flow circuit and a reusable hardware component:

a) the disposable fluid flow circuit further comprising i) a spinning membrane separator having housing with a first port/inlet, a second port/filtrate outlet, a third port/retentate outlet, a rotor rotatably supported within the housing, a membrane affixed to the rotor having a porous surface that permits supernatant/plasma and platelets to pass therethrough but not red blood cells and white blood cells, with a gap being defined between the housing and the membrane, ii) a first container of wash media, a second container of lysing buffer, a third container of source media comprising red blood cells and white blood cells, a fourth container for receiving retentate and a fifth container for receiving waste/filtrate; iii) a flow control cassette for directing fluid flow from the first, second and third containers through the spinning membrane separator and to the fourth and fifth containers, the flow control cassette further including a) internal flow paths in fluid communication with each of the first-fifth containers and the first-third ports of the spinning membrane separator, b) valves/clamps associated with the fluid flow paths for controlling flow therethrough, and c) interface detectors;

b) the reusable hardware component comprising first and second pumps for moving fluid from the first-third containers through the flow paths in the flow control cassette and into the fourth and fifth containers, volume sensors associated with each of the first and second pumps for measuring the volume of fluid pumped, a weigh scale associated with each of the first-fifth containers, and a programmable controller programmed to automatically perform the method of claim 1 based on signals received from the interface detectors and one or both of the volume sensors associated with the pumps and the weigh scales associated with the first-fifth containers.

9. The system of claim 8 wherein each of the first and second pumps comprises a syringe pump and the volume sensors comprise position detectors associated with each syringe pump.

* * * * *